(12) United States Patent
Cornish et al.

(10) Patent No.: US 6,440,421 B1
(45) Date of Patent: Aug. 27, 2002

(54) TREATMENT OF BONE DISORDERS WITH ADRENOMEDULLIN OR ADRENOMEDULLIN AGONISTS

(75) Inventors: Jillian Cornish; Ian Reginald Reid; Garth James Smith Cooper, all of Auckland (NZ)

(73) Assignee: Auchkland Uniservices Limited, Auckland (NZ)

( * ) Notice: Subject to any disclaimer, the term of this patent is extended or adjusted under 35 U.S.C. 154(b) by 0 days.

(21) Appl. No.: 09/280,501

(22) Filed: Mar. 30, 1999

Related U.S. Application Data

(63) Continuation-in-part of application No. 08/634,562, filed on Apr. 18, 1996, now Pat. No. 5,888,963.
(51) Int. Cl.$^7$ ............................................. A61K 39/00
(52) U.S. Cl. ............................... 424/198.1; 424/185.1; 530/328
(58) Field of Search ......................... 424/198.1, 185.1; 530/328

(56) References Cited

U.S. PATENT DOCUMENTS 5,478,847 A 12/1995 Draper

FOREIGN PATENT DOCUMENTS

| EP | 0 622 458 A2 | 11/1994 | |
|---|---|---|---|
| WO | WO 97 07214 A | 2/1997 | |
| WO | WO 97/38704 | 10/1997 | .......... A61K/38/00 |
| WO | WO 99/16406 | 4/1999 | |

OTHER PUBLICATIONS

The Merck Manual of Diagnosis and Therapy, 17$^{th}$ Edition pp. 469–473, 1999.*
Ngo et al. The Protein Folding Problem and Tertiary Structure Prediction. pp. 433 & 492–495, 1994.*
Cornish et al., "Adrenomedullin is a Potent Stimulator of Osteoblastic Activity In Vitro and In Vivo", American Physiological Society,, (1997), 273, pp. E1113–E1120.
Wimalawansa et al., "Amylin, Calcitonin Gene–Related Peptide, Calcitonin, and Adrenomedullin: A Peptide Superfamily", Critical Reviews in Neurobiology 11:167–239, 1997.
Cheng et al., "Synthetic Human Adrenomedullin and ADM15–52 Have Potent Short–Lasting Vasodilator Activity In The Pulmonary Vascular Bed of the Cat", Life Sciences, 55:PL251–PL256, 1994.
Cornish et al., BBRC, 207(1): 133–139, 1995.
DeWitt et al., European J. Pharmacol., 257:303–306, 1996.
Eguchi et al., "Structure–Activity Relationship of Adrenomedullin, a Novel Vasodilatory Peptide, in Cultured Rat Vascular Smooth Muscle Cells", Endrocrinology, 135:2454–2458, 1994.

Hao et al., "An Adrenomedullin (ADM) Fragment Retains the Systemic Vasodilator Activity of Human ADM", Life Sciences, 54:PL265–PL270, 1994.
Ichiki et al., "Distribution and Characterization of Immunoreactive Adrenomedullin in Human Tissue and Plasma", FEBS Letters, 338:6–10, 1994.
Ishiyama et al., "Hemodynamic Effects of a Novel Hypotensive Peptide, Human Adrenomedullin, In Rats", European Journal of Pharmacology, 241:271–273, 1993.
Kanazawa et al., "Adrenomedullin, A Newly Discovered Hypotensive Peptide, Is a Potent Bronchodilator", 205:251–254, 1994.
Kitamura et al., "Adrenomedullin: A Novel Hypotensive Peptide Isolated From Human Pheochromocytoma", Biochemical & Biophysical Research Comm., 192:553–560, 1993.
Kitamura et al., "Cloning and Characterization of cDNA Encoding a Precursor for Human Adrenomedullin", Biochemical & Biophysical Research Comm., 194:720–725, 1993.
Kitamura et al., "Complete Amino Acid Sequence of Porcine Adrenomedullin and Cloning of cDNA Encoding its Precursor", FEBS Letters, 338:306–310, 1994.
Lin et al., "An Adrenomedullin Fragment Retains the Systemic Vasodepressor Activity of Rat Adrenomedullin", European Journal of Pharmacology, 260:1–4, 1994.
Lippton et al., "Adrenomedullin Dilates the Pulmonary Vascular Bed In Vivo", J. Appl. Physiol., 76:2154–2156, 1994.
Muff et al., "Calcitonin, Calcitonin Gene–related Peptide, Adrenomedullin and Amylin: Homologous Peptides, Separate Receptors and Overlapping Biological Actions", European Journal of Endocrinology, 133:17–20, 1995.
Nuki et al., "Vasodilator Effect of Adrenomedullin and Calcitonin Gene–Related Peptide Receptors In Rat Mesenteric Vascular Beds", Biochemical and Biophysical Research Comm., 196:245–251, 1993.
Owji et al., "An Abundant and Specific Binding Site for the Novel Vasodilator Adrenomedullin in the Rat", Endocrinology, 136:2127–2134, 1995.
Perret et al., "The Effect of Adrenomedullin on the Isolated Heart", Life Sciences, 53:PL377–379, 1993.
Sakata et al., "Molecular Cloning and Biological Activities of Rat Adrenomedullin, A Hypotensive Peptide", Biochemical and Biophysical Research Comm., 195:921–927, 1993.

(List continued on next page.)

Primary Examiner—Patrick J. Nolan
(74) Attorney, Agent, or Firm—Fish & Richardson PC

(57) ABSTRACT

A method for promoting bone growth in a patient (e.g., a mammal such as a human) said method including the step of administering a therapeutically effective amount of adrenomedullin or an adrenomedullin agonist to said patient.

10 Claims, No Drawings

OTHER PUBLICATIONS

Santiago et al., "Comparison of Responses to Adrenomedullin and Adrenomedullin Analogs in the Mesenteric Vascular Bed of the Cat", *European Journal of Pharmacology*, 272:115–118, 1995.

Santiago et al., "Synthetic Human Adrenomedullin and Adrenomedullin 15–52 Have Potent Short–Lived Vasodilator Activity in the Hindlimb Vascular Bed of the Cat", *Life Sciences*, 55:PL85–PL90, 1994.

Zimmerman et al., "Adrenomedullin and Calcitonin Gene–Related Peptide Interact With the Same Receptor in Cultured Human Neuroblastoma SK–N–MC Cells", *Peptides*, 16:421–424, 1995.

GenBank Accession No. AAW25159: Dec. 8, 1997.

Belloni et al., "Inhibitory Effect of Adrenomedullin (ADM) on the Aldosterone . . . . . . .", 1998, Life Sciences, vol. 63, No. 26;2313–2321.

Cornish et al., "Systemic administration of adrenomedullin (27–52) increases . . . .", 2001, J. Endocrinology, vol. 170;251–257.

Cornish et al., "Skeletal Effects of Amylin . . . . . . .", 1999, Endocrinologist; 183–189.

Watanabe et al., "Vasopresser Activities of N–Terminal Fragments . . . . . . .", 1996, Biochem and Biophysical Research Commun., vol. 219;59–63.

* cited by examiner

TREATMENT OF BONE DISORDERS WITH ADRENOMEDULLIN OR ADRENOMEDULLIN AGONISTS

CROSS REFERENCE TO RELATED APPLICATIONS

This application is a continuation-in-part of U.S. Ser. No 08/634,562, now U.S. Pat. No. 5,888,963 filed Apr. 18, 1996.

FIELD OF THE INVENTION

This invention relates to a method of promoting bone growth in a patient.

BACKGROUND OF THE INVENTION

Adrenomedullin is a 52-amino acid peptide originally identified in a human pheochromocytoma. It has since been found in normal adrenal medulla, as well as other tissues such as the atria, ventricles, endothelial cells, lungs, brain and kidneys. Adrenomedullin also circulates in picomolar concentrations in both rats and man.

Several biological effects have been attributed to adrenomedullin. It has been described as a potent vasodilator, acting directly on the renal, cerebral, mesenteric, pulmonary, and systemic circulations. Administration of adrenomedullin can result in hypotension.

Binding of adrenomedullin to renal tubular membranes has also been observed, and sodium, potassium, and water excretion are increased by adrenomedullin. Adrenomedullin can in addition be a bronchodilator, and it has been reported to modulate the release of pituitary and vasoactive hormones.

SUMMARY OF THE INVENTION

The present invention is based on the discovery that adrenomedullin and peptide fragments of adrenomedullin can stimulate proliferation of osteoblasts, which give rise to bone tissue. Accordingly, the invention provides methods for promoting bone growth, and compositions useful for promoting bone growth.

In one aspect the invention provides a method for promoting bone growth in a patient, e.g., a mammal such as a human. The method includes the step of administering a therapeutically effective amount of adrenomedullin or an adrenomedullin agonist to the patient. The patient may be suffering from a disease associated with excessive resorption or breakdown of bone tissue such as osteoporosis or Paget's disease. The patient may also be suffering from bone losses as a result of immobility, bone fractures, malignancy, endocrine disorders, autoimmune arthritis, or drug use. The patient may also be undergoing a treatment (e.g., corticosteroid treatment, bone marrow transplantation, or oophorectomy) known to result in bone loss.

In another aspect, the invention features a method for prevent or retarding the development of a bone-associated diseases in a subject, e.g. a mammalian subject such as a human. Thus, the adrenomedullin and adrenomedullin agonists described herein may be used, e.g., to prevent development of osteoporosis or Paget's disease in a subject.

A therapeutically effective amount depends upon the condition being treated, the route of administration chosen, and the specific activity of the compound used and ultimately will be decided by the attending physician or veterinarian. In one embodiment, the adrenomedullin agonist is administered to the patient until the patient's bone mass has been restored to normal levels. Thus, the duration of the administration may be dependent upon the severity of the patient's bone loss.

The adrenomedullin or adrenomedullin agonist may be administered parenterally, e.g., administered intravenously, subcutaneously, or by implantation of a sustained release formulation. However, it will be readily appreciated by those skilled in the art that the route, such as intravenous, subcutaneous, intramuscular, intraperitoneal, enterally, transdermally, transmucously, sustained released polymer compositions (e.g., a lactide polymer or copolymer microparticle or implant), profusion, pulmonary (e.g., inhalation), nasal, oral, etc., will vary with the condition being treated and the activity and bioavailability of the adrenomedullin or adrenomedullin agonist being used.

While it is possible for the adrenomedullin or adrenomedullin agonist to be administered as the pure or substantially pure compound, it may also be presented as a pharmaceutical formulation or preparation. The formulations to be used in the present invention, for both humans and animals, comprise any of the adrenomedullin or adrenomedullin agonists to be described below, together with one or more pharmaceutically acceptable carriers thereof, and optionally other therapeutic ingredients.

The carrier must be "acceptable" in the sense of being compatible with the active ingredient(s) of the formulation (e.g., capable of stabilizing peptides) and not deleterious to the subject to be treated. Desirably, the formulation should not include oxidizing agents or other substances with which peptides are known to be incompatible. For example, adrenomedullin or adrenomedullin agonists in the cyclized form (e.g., internal cysteine disulfide bond) are oxidized; thus, the presence of reducing agents as excipients could lead to an opening of the cysteine disulfide bridge. On the other hand, highly oxidative conditions can lead to the formation of cysteine sulfoxide and to the oxidation of tryptophane. Consequently, it is important to carefully select the excipient. Ph is another key factor, and it may be necessary to buffer the product under slightly acidic conditions (Ph 5 to 6).

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary, as in the case of tablets, forming the product into the desired shape and size.

Formulations suitable for parenteral (e.g., intravenous) administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Formulations suitable for sustained release parenteral administrations (e.g., biodegradable polymer formulations) are also well known in the art. See, e.g., U.S. Pat. Nos. 3,773,919 and 4,767,628 and PCT Publication No. WO 94/15587.

The adrenomedullin or adrenomedullin agonist may also be administered with an bone anti-resorptive agent or another bone anabolic agent. Examples of bone anti-resorptive agents include calcitonin, bisphosphonates (e.g., etidronate, alendronate, or pamidronate), estrogen, and analogs thereof. Examples of bone anabolic agents include parathyroid hormone, parathyroid hormone related protein, cytokines (e.g., TGF-β,IGF-1), growth hormone, and analogs thereof.

In another aspect, the invention features a peptide consisting of between 30 and 26 amino acids and comprising the sequence adrenomedullin(27–52) (SEQ ID NO:1) wherein the carboxyl terminal is a free acid or amidated. Examples of such peptides include adrenomedullin(27–52) (SEQ ID NO:1); adrenomedullin(26–52) (SEQ ID NO:2); adrenomedullin(25–52) (SEQ ID NO:3); adrenomedullin (24–52) (SEQ ID NO:4); or adrenomedullin(23–52) (SEQ ID NO:5) wherein the carboxyl terminal is amidated. Peptides of this invention are described herein, for example, by the following format: adrenomedullin(13–52) (SEQ ID NO:11). The numbers between the parentheses refer to the number of amino acids present in the peptide, e.g., the forty amino acid fragment between the serine residue at position 13 and the amidated tyrosine residue at position 52 of adrenomedullin. The sequence of adrenomedullin is listed in FIG. 1 of European Patent Application No. 622,458 A2.

The invention also includes an adrenomedullin (ADM) agonist 5–25, 6–25 or 7–25 amino acids in length. The ADM agonist comprises a fraction or the entirety of the amino acid sequence ADM(32–40) (SEQ ID NO:14). In some embodiments the ADM agonist is 9–25 amino acids in length and includes the amino acid sequence ADM(32–40) (SEQ ID NO:14), e.g., the ADM agonist can include the amino acid sequences ADM (28–40) (SEQ ID NO:15), ADM(32–52) (SEQ ID NO:16), and ADM (30–52) (SEQ ID NO:17). Other examples of ADM agonists include peptides 10–25, 12–22, or 13–23 amino acids in length and containing the amino acid sequence ADM(32–40) (SEQ ID NO:14).

The ADM agonists described herein are useful in treating diseases for which increased osteoblast proliferation is desirable. Thus, the ADM agonists are useful for treating bone-associated conditions or diseases such as osteoporosis and Paget's disease and in preventing or inhibiting the development of such bone-associated diseases in subjects at risk for developing these diseases.

Other features and advantages of the invention will be apparent from the following description of the preferred embodiments and from the claims.

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

Adrenomedullin and Adrenomedullin Agonists

Adrenomedullin is a 52-amino acid having an amidated C-terminus. Many analogs, e.g., carboxyl terminal fragments, have been prepared, such as adrenomedullin (15–52) (SEQ ID NO:6), adrenomedullin(1–50) (SEQ ID NO:7), adrenomedullin(11–50) (SEQ ID NO:8), adrenomedullin(22–52) (SEQ ID NO:9), adrenomedullin (40–52) (SEQ ID NO:10), adrenomedullin(13–52) (SEQ ID NO:11), adrenomedullin(47–52) (SEQ ID NO:12), and adrenomedullin(45–52) (SEQ ID NO:13). See European Patent No. 622,458 A2; Lin, et al., Eur. J. Pharmacol. 260:1–4 (1990); and Santiago, J. A., et al., Eur. J. of Pharmacology 272:115–118 (1995). What is meant by an adrenomedullin agonist is a compound which (1) has a high affinity (e.g., a Ki of less than 1 μM) for the adrenomedullin receptor (as defined by the receptor binding assay described in Owji, et al., Endocrinology 136(5):2128 (1995)) and (2) promotes the proliferation of osteoblast cells (as defined below in the osteoblast proliferation assays).

Synthesis

The synthesis of short amino acid sequences is well established in the peptide art. See, e.g., Stewart, et al., Solid Phase Peptide Synthesis (2d ed., 1984). The following is the synthesis of adrenomedullin (27–52) (SEQ ID NO:1). Other such adrenomedullin agonists can be prepared by making appropriate modifications, within the ability of someone of ordinary skill in the field of the synthetic method described herein.

Benzhydrylamine-polystyrene resin (Advanced ChemTech, Inc., Louisville, Ky.) (0.6 g, 0.25 mmole) in the chloride ion form was placed in the reaction vessel of an Advanced ChemTech peptide synthesizer programmed to perform the following reaction cycle: (a) methylene chloride; (b) 33% trifluoroacetic acid in methylene chloride (2 times for 1 and 15 min each); (c) methylene chloride; (d) ethanol; (e) methylene chloride; and (f) 10% diisopropylethylamine in methylene chloride.

The neutralized resin was stirred with Boc-Tyr(2,6-dichlorobenzyl) and diisopropylcarbodiimide (0.75 mmole each) in methylene chloride for 1 h and the resulting amino acid resin was then cycled through steps (a) to (f) in the above wash program. The following amino acids (0.75 mmole) were then coupled successively by the same procedure: Boc-Gly, Boc-Gln, Boc-Pro, Boc-Ser(benzyl), Boc-Ile, Boc-Lys(2-chloro-CBZ), Boc-Ser(benzyl), Boc-Arg(p-Tosyl), Boc-Pro, Boc-Ala, Boc-Ala, Boc-Val, Boc-Asn, Boc-Asp(cyclohexyl), Boc-Lys(2-chloro-CBZ), Boc-Asp (cyclohexyl), Boc-Lys(2-chloro-CBZ), Boc-Asp (cyclohexyl), Boc-Thr(benzyl), Boc-Phe, Boc-Gln, Boc-Tyr (2,6-dichlorobenzyl), Boc-Ile, Boc-Gln, Boc-His (benzyloxymethyl), and Boc-Ala. After removal of the last Boc group and washing and drying, the completed resin weighed 1.11 g. All amino acids were purchased from Bachem California, (Torrence, Calif.).

The resin described above (1.11 g, 0.25 mmole) was mixed with anisole (5 ml), dithiothreitol (100 mg) and anhydrous hydrogen fluoride (35 ml) at 0° C. and stirred for 45 min. Excess hydrogen fluoride was evaporated rapidly under a stream of dry nitrogen, and free peptide precipitated and was washed with ether. The crude peptide was then dissolved in a minimum volume of 2 M acetic acid and eluted on a column (2.5×100 cm) of Sephadex G-50 (Pharmacia, Piscataway, N.J.) using the same solvent. Fractions containing a major component, detected by ultraviolet absorption and thin layer chromatography, were then pooled, evaporated to a small volume, and applied to a column (2.5×50 cm) of Vydac octadecylsilane silica (10–15 μ; Rainin, Emeryville, Calif.). This column was eluted with a linear gradient of 10–45% acetonitrile in 0.1% trifluoroacetic acid in water. Fractions were examined by thin layer chromatography (tlc) and analytical high performance liquid chromatography (hplc) and pooled to give maximum purity. Repeated lyophilization of the solution from water gave the product as the amide and as a white, fluffy power. The product is found to be homogeneous by hplc and tlc. Amino acid analysis of an acid hydrolysate confirmed the composition of the peptide. Laser desorption mass spectroscopy gave the expected molecular weight.

In vitro studies

Adrenomedullin agonists can be tested for their ability to promote bone growth by examining their activity in the in vitro and in vivo assays described herein.

Osteoblast Cell Culture

Osteoblasts were isolated by collagenase digestion from 20-day fetal rat calvariae. The calvariae were then treated twice with phosphate buffered saline (PBS; Gibco, Grand Island, N.Y.) containing 3 Mm ethylene diamine-acetic acid (EDTA; Sigma Chemical Co., St. Louis, Mo.) for 15 minutes at 37° C. in a shaking water bath. After washing once in PBS, 3 ml of 1 mg/ml collagenase (Sigma Chemical Co.) was added to the calvariae for 10 minutes at 37° C. After discarding the supernatant, the calvariae were treated twice with 2 mg/ml collagenase (30 mins, 37° C.). The supernatants were then centrifuged and the cells washed in Dulbecco's Modified Eagle's Medium (DMEM; Gibco Labs, Grand Island, N.Y.) with 10% fetal calf serum (FCS), suspended in further DMEM/10% FCS, and placed in 75 $cm^3$ flasks. The cells were incubated under 5% $CO_2$ and 95% air at 37° C.

The osteoblast-like character of these cells has been established by demonstration of high levels of alkaline phosphatase and osteocalcin, and a sensitive adenylate cyclase response to parathyroid hormone and prostaglandins. Confluence was reached by 5–6 days, at which time the cells were subcultured. After trypsinization using trypsin-EDTA (0.05%/0.53 Nm; Gibco Labs, Grand Island, N.Y.), the cells were rinsed in Minimal Essential Medium (MEM; Gibco Labs) with 10% FCS and resuspended in MEM with 5% FCS, then seeded ($10^5$ cells/ml) in 24-well plates (0.5 ml cell suspension per well, i.e., $5 \times 10^4$ cells/well)

Proliferation Assays

Cell proliferation studies (i.e., cell counts and thymidine incorporation) were performed both in actively-growing and growth-arrested cell populations. To produce actively-growing cells, subconfluent populations (24 hrs after subculturing) were changed to fresh MEM which contained 1% FCS and the test compounds. To produce growth-arrested cells, subconfluent populations were changed to serum-free medium with 0.1% bovine serum albumin plus the test compounds.

A. Cell Counts

The effect of adrenomedullin on proliferation of fetal rat osteoblast-like cells was first assessed by the measurement of cell numbers. Cell counts were analyzed at 6, 24, and 48 hours after addition of the test compound or vehicle. The cell numbers were determined after removing cells from the wells by exposure to trypsin/EDTA (0.05%/0.53 Mm) for 5 minutes at 37° C. Counting was performed in a hemocytometer chamber. Results were expressed per well. Treatment with adrenomedullin for 24 hours, in cultures grown in medium containing 1% FCS, produced a dose-dependent increase in actively-growing osteoblasts. A significant increase was observed at adrenomedullin concentrations of $10^{-12}$M and greater. This stimulation was maintained for at least 48 hours.

To determine whether proliferation in response to adrenomedullin was dependent on the basal growth rate of the cells, these experiments were repeated in growth-arrested osteoblast preparations. The time-course of the increase in cell number in response to adrenomedullin ($10^{-10}$M) in these cells was similar to that seen in actively-growing cells.

Treatment for 24 hrs with the test compounds adrenomedullin(15–52) (SEQ ID NO:6), adrenomedullin (22–52) (SEQ ID NO:9), and adrenomedullin(27–52) (SEQ ID NO:1) produced similar degrees of proliferation to that of the fill length adrenomedullin polypeptide.

B. DNA Synthesis

The effect of adrenomedullin on DNA synthesis in osteoblasts was then assessed by the measurement of [$^3$H]-thymidine incorporation into isolated fetal rat osteoblast-like cells. [$^3$H]-thymidine incorporation into actively-growing and growth-arrested cells was assessed by pulsing the cells with [$^3$H]-thymidine (1 $\mu$Ci/ml) (Amersham, Arlington Heights, Ill.) two hours before the end of the experimental incubation. The experiment was terminated at 6, 24, or 48 hours by washing the cells in MEM with cold thymidine followed by 10% trichloroacetic acid. The precipitate was washed twice with ethanol:ether (3:1), and the wells were desiccated at room temperature. The residue was redissolved in 0.5 M KOH at 85° C. for 30 mins, neutralized with 1 M Hcl, and an aliquot counted for radioactivity. Results were expressed as cpm per well.

Treatment with adrenomedullin ($10^{-10}$M) for 24 hours significantly stimulated [$^3$H]-thymidine incorporation into both actively-growing and growth-arrested cells.

The effect of adrenomedullin fragments on proliferation of primary cultures of osteoblasts was also tested. Addition of either ADM(28–40) (SEQ ID NO:15), ADM(32–52) (SEQ ID NO:16), ADM (28–40) (SEQ ID NO:15), and ADM (27–52) (SEQ ID NO:1) to a final concentration of 1 nm produced a statistically significant increase in cell number relative to control osteoblasts. Thymidine incorporation was also increased in osteoblasts treated with 1 nm of these fragments.

Bone Organ Culture

Bone resorption studies were carried out in neonatal mouse calvariae as previously described (Reid, et al., Endocrinology 126:1416–1420 (1990)). Mice were injected subcutaneously with 5 $\mu$Ci $^{45}$Ca (Amersham) at 2 days of age, and hemi-calvariae were dissected out 4 days later. Hemi-calvariae were pre-incubated for 24 hours in medium 199 (Gibco BRL, Grand Island, N.Y.) with 0.1% bovine serum albumin, then changed to fresh medium containing adrenomedullin or control vehicle. Incubation was continued for a further 48 hours. In the last 4 hours of incubation [$^3$H]-thymidine was incorporated into the organ cultures as described previously (Lowe, et al., Calif. Tissue Int. 49-394–397 (1991)). There were 5–7 calvariae in each group.

There was no significant change in $^{45}$Ca release from prelabeled calvariae treated for 48 hours with adrenomedullin at concentrations of 10–7 M to $10^{-10}$ M indicating that adrenomedullin did not stimulate bone resorption. In contrast, [$^3$H]-thymidine incorporation was significantly increased in the same experiments indicating that adrenomedullin stimulated bone growth.

In vivo Studies

The local effects of adrenomedullin on bone histology in vivo were assessed in adult mice using a previously described model (Cornish et al., Endocrinology 132:1359–1366, 1993). Sexually mature male ARC Swiss Webster mice aged between 40 and 50 days and weighing 25–35 were given injections (25 $\mu$l) over the periosteum of the right hemicalvariae for 5 consecutive days. Previous studies with dye injections have shown that the injected material spreads over much of the injected hemicalvariae but does not cross the midline. The animals were maintained on a low calcium diet (0.1%) from 5 days prior to the first injection. Two groups of mice (n=12 in each) were injected daily with adrenomedullin in doses of $4\times10^{-10}$ M and 4×10−9 M, respectively. These doses were chosen based on experience with other bone-active peptides in this model. Animals in the control group (n=16) were injected with vehicle (water) only. All animals were sacrificed 1 week following the last injection. The study had the approval of the local institutional review board.

The calvariae were dissected free of soft tissue, and gross morphology was assessed by examination of the intact calvariae under a dissection microscope. Bone tissue was fixed in 10% phosphate-buffered formalin, dehydrated in a graded series of ethanol solutions and embedded undecalcified in methyl methacrylate resin. Sections (4 $\mu$m thick) were cut on a Leitz rotary microtome (Leica Instruments, Nussloch, Germany) using a tungsten-carbide knife, then mounted on gelatin-coated slides and air-dried. The sections were stained with a Goldner tri-chrome stain and examined using an Olympus BX 50 microscope (Olympus Optical Co Ltd, Tokyo, Japan) which was attached to an Osteomeasure Image Analyzer (Osteometrics Inc., Atlanta, Ga.). Histomorphometric analyzes were made of three adjacent fields (using a 20× objective) in each hemicalvaria. This results in measurements being made over >90% of the length of each hemicalvaria.

The parameters assessed are as defined by the American Society for Bone and Mineral Research (Parfitt et al. J. Bone Miner. Res. 2:595–610, (1987)), and are expressed per mm of calvarial length. Osteoblasts were defined as cells immediately adjacent to osteoid. Osteoclast numbers included only multinucleated cells. The various surface estimates were based on measurements of both periosteal and intramembranous surfaces: those eroded by osteoclasts (eroded perimeter), those immediately adjacent to osteoclasts (osteoclast perimeter), and those immediately adjacent to osteoblasts (osteoblast perimeter). The precision of these histomorphometric measurements in these studies (expressed as coefficients of variation of paired. measurements) are as follows: mineralized bone area 1.3%, osteoid area 6.9%, osteoblast perimeter 6.8%, osteoblast number 1.7%, eroded perimeter 6.7%, osteoclast perimeter 7.9%, osteoclast number <1.0%, and calvarial length 0.2%. All measurements were made by one operator who was blinded to the treatment group of each bone.

In the in vivo experiment, the primary end-point for each histomorphometric index was the determination of whether it was different in the injected right hemicalvaria from the contralateral, uninjected bone of the same animal. The absolute values of each histomorphometric index are presented for the injected and uninjected hemicalvariae by treatment group in Tables 1–3. The tables set out the histomorphometric indices in the uninjected and injected hemicalvariae from each of three groups: mice injected with vehicle (Table 1), mice injected with $4\times10^{-10}$ M adrenomedullin (Table 2), or mice injected with $4\times10^{-9}$ M adrenomedullin (Table 3). Statistical analysis performed on the ratios of each index in the injected to the uninjected halves of each calvariae revealed two- to three-fold increases in the indices of osteoblast activity in those bones exposed to either dose of adrenomedullin. Resorption indices showed slight upward trends in the presence of adrenomedullin but only for eroded perimeter was this significant. Mineralized bone area was increased by 13.6% with the higher dose of adrenomedullin. Periosteal area was not changed (P=0.54). Tables 1–3. Effects of Adrenomedullin on Histomorphometric Indices in Adult Mouse Calvariae in vivo*

TABLE 1

| | Vehicle | |
| --- | --- | --- |
| Index | Uninjected | Injected |
| Osteoid Area | 0.0025 (0.0004) | 0.0021 (0.0003) |
| Ob Perimeter | 0.69 (0.10) | 0.76 (0.07) |
| Number of Obs | 65 (8) | 68 (5) |
| Eroded Pm | 0.74 (0.10) | 0.76 (0.10) |
| Oc Pm | 0.12 (0.01) | 0.13 (0.02) |
| Number of Ocs | 4.4 (0.3) | 4.5 (0.3) |
| Periosteal Area | 0.014 (0.002) | 0.013 (0.001) |
| Bone Area | 0.113 (0.005) | 0.106 (0.005) |

TABLE 2

| | Adrenomedullin $4 \times 10^{-10}$ mol | |
| --- | --- | --- |
| Index | Uninjected | Injected |
| Osteoid Area | 0.0016 (0.0003) | 0.0041 (0.0005) |
| Ob Perimeter | 0.72 (0.10) | 1.21 (0.13) |
| Number of Obs | 57 (5) | 111 (11) |
| Eroded Pm | 0.77 (0.13) | 0.85 (0.09) |
| Oc Pm | 0.12 (0.02) | 0.14 (0.01) |
| Number of Ocs | 4.4 (0.4) | 5.2 (0.3) |
| Periosteal Area | 0.013 (0.002) | 0.015 (0.001) |
| Bone Area | 0.115 (0.005) | 0.122 (0.006) |

TABLE 3

| | Adrenomedullin $4 \times 10^{-10}$ mol | |
| --- | --- | --- |
| Index | Uninjected | Injected |
| Osteoid Area | 0.0012 (0.0002) | 0.0032 (0.0008) |
| Ob Perimeter | 0.56 (0.06) | 0.33 (0.09) |
| Number of Obs | 61 (5) | 105 (6) |
| Eroded Pm | 0.67 (0.08) | 0.67 (0.07) |
| Oc Pm | 0.12 (0.01) | 0.15 (0.01) |
| Number of Ocs | 4.4 (0.3) | 5.0 (0.3) |
| Periosteal Area | 0.011 (0.001) | 0.012 (0.002) |
| Bone Area | 0.114 (0.006) | 0.128 (0.007) |

*Data are mean (se). Ob, osteoblast; Pm, perimeter; Oc, osteoclast

Other Embodiments

It is to be understood that while the invention has been described in conjunction with the detailed description thereof, that the foregoing description is intended to illustrate and not limit the scope of the invention, which is defined by the scope of the appended claims. For example, the adrenomedullin agonists described herein may include amino acids linked via non-peptidyl linkages, e.g., a peptide in which one or more peptide bonds have a carbonyl oxygen replaced with a methylene group. The adrenomedullin agonists may alternatively or in addition include amino acids other than the encoded amino acids. These include, e.g., substitution of the naturally occurring L-form of an encoded amino acid with its corresponding D-form. Other aspects, advantages, and modifications are within the claims.

What is claimed is:

1. A method of promoting bone growth in a patient, said method comprising administering to a patient in need thereof an ADM agonist 7–25 amino acids in length, wherein said ADM agonist comprises the amino acid sequence ADM(32–40) (SEQ ID NO:14) or a fraction thereof.

2. The method of claim 1, wherein said ADM agonist is amidated at its carboxyl terminus.

3. The method of claim 1, wherein said patient suffers from osteoporosis.

4. A method of promoting bone growth in a subject at risk for developing a bone-associated disease, said method comprising administering to a subject in need thereof an ADM agonist 7–25 amino acids in length, wherein said ADM agonist comprises the amino acid sequence ADM(32–40) (SEQ ID NO:14) or a fraction thereof.

5. The method of claim 4, wherein said ADM agonist is amidated at its carboxyl terminus.

6. The method of claim 4, wherein said subject is at risk for osteoporosis.

7. The method of claim 1, wherein said ADM agonist is 9–25 amino acids in length and comprises the amino acid sequence ADM(32–40) (SEQ ID NO:14) or a fraction thereof.

8. The method of claim 1, wherein said ADM agonist is ADM(32–40) (SEQ ID NO:14), ADM(28–40) (SEQ ID NO:15), ADM(32–52) (SEQ ID NO:16), or ADM(30–52) (SEQ ID NO:17).

9. The method of claim 4, wherein said ADM agonist is 9–25 amino acids in length and comprises the amino acid sequence ADM(32–40) (SEQ ID NO:14) or a fraction thereof.

10. The method of claim 4, wherein said ADM agonist is ADM(32–40) (SEQ ID NO:14), ADM(28–40) (SEQ ID NO:15), ADM(32–52) (SEQ ID NO:16), or ADM(30–52) (SEQ ID NO:17).

* * * * *

UNITED STATES PATENT AND TRADEMARK OFFICE
CERTIFICATE OF CORRECTION

PATENT NO. : 6,440,421 B1  
DATED : August 27, 2002  
INVENTOR(S) : Jillian Cornish, Garth James Smith Cooper and Ian Reginald Reid Page 1 of 1

It is certified that error appears in the above-identified patent and that said Letters Patent is hereby corrected as shown below:

<u>Title page,</u>
Item [73], Assignee, "Auchkland" should be -- Auckland --.
Item [56], OTHER PUBLICATIONS, "Cornish et al." reference, "American Physiological Society,, (1997)" should be -- American Physiological Society, (1997) --.

<u>Column 1,</u>
Line 57, "prevent" should be -- preventing --.
Line 57, delete the "a" before "bone-associated".

<u>Column 3,</u>
Line 2, "an" should be -- a --.

<u>Column 6,</u>
Line 8, "fill" should be -- full --.
Lines 29-37, correct left margin.
Line 55, "10-7" should be -- $10^{-7}$ --.
Line 66, after "25-35" insert -- g --.

<u>Column 7,</u>
Line 7, "10-9" should be -- $10^{-9}$ --.

<u>Column 8,</u>
Line 34, "$10^{-10}$" should be -- $10^{-9}$ --.
Line 38, "0.33" should be -- 1.33 --.

Signed and Sealed this

Twenty-eighth Day of October, 2003

JAMES E. ROGAN  
*Director of the United States Patent and Trademark Office*

SEQUENCE LISTING

<160> NUMBER OF SEQ ID NOS: 17

<210> SEQ ID NO 1
<211> LENGTH: 26
<212> TYPE: PRT
<213> ORGANISM: Homo sapiens

<400> SEQUENCE: 1

Ala His Gln Ile Tyr Gln Phe Thr Asp Lys Asp Lys Asp Asn Val Ala
 1               5                  10                  15

Pro Arg Ser Lys Ile Ser Pro Gln Gly Tyr
            20                  25

<210> SEQ ID NO 2
<211> LENGTH: 27
<212> TYPE: PRT
<213> ORGANISM: Homo sapiens

<400> SEQUENCE: 2

Leu Ala His Gln Ile Tyr Gln Phe Thr Asp Lys Asp Lys Asp Asn Val
 1               5                  10                  15

Ala Pro Arg Ser Lys Ile Ser Pro Gln Gly Tyr
            20                  25

<210> SEQ ID NO 3
<211> LENGTH: 28
<212> TYPE: PRT
<213> ORGANISM: Homo sapiens

<400> SEQUENCE: 3

Lys Leu Ala His Gln Ile Tyr Gln Phe Thr Asp Lys Asp Lys Asp Asn
 1               5                  10                  15

Val Ala Pro Arg Ser Lys Ile Ser Pro Gln Gly Tyr
            20                  25

<210> SEQ ID NO 4
<211> LENGTH: 29
<212> TYPE: PRT
<213> ORGANISM: Homo sapiens

<400> SEQUENCE: 4

Gln Lys Leu Ala His Gln Ile Tyr Gln Phe Thr Asp Lys Asp Lys Asp
 1               5                  10                  15

Asn Val Ala Pro Arg Ser Lys Ile Ser Pro Gln Gly Tyr
            20                  25

<210> SEQ ID NO 5
<211> LENGTH: 30
<212> TYPE: PRT
<213> ORGANISM: Homo sapiens

<400> SEQUENCE: 5

Val Gln Lys Leu Ala His Gln Ile Tyr Gln Phe Thr Asp Lys Asp Lys
 1               5                  10                  15

Asp Asn Val Ala Pro Arg Ser Lys Ile Ser Pro Gln Gly Tyr
            20                  25                  30

<210> SEQ ID NO 6
<211> LENGTH: 38
<212> TYPE: PRT
<213> ORGANISM: Homo sapiens

-continued

<400> SEQUENCE: 6

Gly Cys Arg Phe Gly Thr Cys Thr Val Gln Lys Leu Ala His Gln Ile
1               5                   10                  15

Tyr Gln Phe Thr Asp Lys Asp Lys Asp Asn Val Ala Pro Arg Ser Lys
                20                  25                  30

Ile Ser Pro Gln Gly Tyr
            35

<210> SEQ ID NO 7
<211> LENGTH: 50
<212> TYPE: PRT
<213> ORGANISM: Homo sapiens

<400> SEQUENCE: 7

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
                20                  25                  30

Phe Thr Asp Lys Asp Lys Asp Asn Val Ala Pro Arg Ser Lys Ile Ser
                35                  40                  45

Pro Gln
    50

<210> SEQ ID NO 8
<211> LENGTH: 40
<212> TYPE: PRT
<213> ORGANISM: Homo sapiens

<400> SEQUENCE: 8

Leu Arg Ser Phe Gly Cys Arg Phe Gly Thr Cys Thr Val Gln Lys Leu
1               5                   10                  15

Ala His Gln Ile Tyr Gln Phe Thr Asp Lys Asp Lys Asp Asn Val Ala
                20                  25                  30

Pro Arg Ser Lys Ile Ser Pro Gln
            35                  40

<210> SEQ ID NO 9
<211> LENGTH: 31
<212> TYPE: PRT
<213> ORGANISM: Homo sapiens

<400> SEQUENCE: 9

Thr Val Gln Lys Leu Ala His Gln Ile Tyr Gln Phe Thr Asp Lys Asp
1               5                   10                  15

Lys Asp Asn Val Ala Pro Arg Ser Lys Ile Ser Pro Gln Gly Tyr
                20                  25                  30

<210> SEQ ID NO 10
<211> LENGTH: 13
<212> TYPE: PRT
<213> ORGANISM: Homo sapiens

<400> SEQUENCE: 10

Asn Val Ala Pro Arg Ser Lys Ile Ser Pro Gln Gly Tyr
1               5                   10

<210> SEQ ID NO 11
<211> LENGTH: 40
<212> TYPE: PRT
<213> ORGANISM: Homo sapiens

<400> SEQUENCE: 11

Ser Phe Gly Cys Arg Phe Gly Thr Cys Thr Val Gln Lys Leu Ala His
1               5                   10                  15

Gln Ile Tyr Gln Phe Thr Asp Lys Asp Lys Asp Asn Val Ala Pro Arg
            20                  25                  30

Ser Lys Ile Ser Pro Gln Gly Tyr
            35                  40

<210> SEQ ID NO 12
<211> LENGTH: 6
<212> TYPE: PRT
<213> ORGANISM: Homo sapiens

<400> SEQUENCE: 12

Ile Ser Pro Gln Gly Tyr
1               5

<210> SEQ ID NO 13
<211> LENGTH: 8
<212> TYPE: PRT
<213> ORGANISM: Homo sapiens

<400> SEQUENCE: 13

Ser Lys Ile Ser Pro Gln Gly Tyr
1               5

<210> SEQ ID NO 14
<211> LENGTH: 9
<212> TYPE: PRT
<213> ORGANISM: Homo sapiens

<400> SEQUENCE: 14

Gln Phe Thr Asp Lys Asp Lys Asp Asn
1               5

<210> SEQ ID NO 15
<211> LENGTH: 13
<212> TYPE: PRT
<213> ORGANISM: Homo sapiens

<400> SEQUENCE: 15

His Gln Ile Tyr Gln Phe Thr Asp Lys Asp Lys Asp Asn
1               5                   10

<210> SEQ ID NO 16
<211> LENGTH: 21
<212> TYPE: PRT
<213> ORGANISM: Homo sapiens

<400> SEQUENCE: 16

Gln Phe Thr Asp Lys Asp Lys Asp Asn Val Ala Pro Arg Ser Lys Ile
1               5                   10                  15

Ser Pro Gln Gly Tyr
            20

<210> SEQ ID NO 17
<211> LENGTH: 23
<212> TYPE: PRT
<213> ORGANISM: Homo sapiens

<400> SEQUENCE: 17

-continued

```
Ile Tyr Gln Phe Thr Asp Lys Asp Lys Asp Asn Val Ala Pro Arg Ser
1               5                   10                  15

Lys Ile Ser Pro Gln Gly Tyr
            20
```